United States Patent
Itu et al.

(10) Patent No.: US 11,389,130 B2
(45) Date of Patent: Jul. 19, 2022

(54) SYSTEM AND METHODS FOR FAST COMPUTATION OF COMPUTED TOMOGRAPHY BASED FRACTIONAL FLOW RESERVE

(71) Applicant: Siemens Healthcare GmbH, Erlangen (DE)

(72) Inventors: Lucian Mihai Itu, Brasov (RO); Saikiran Rapaka, Pennington, NJ (US); Tiziano Passerini, Plainsboro, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 669 days.

(21) Appl. No.: 15/968,836

(22) Filed: May 2, 2018

(65) Prior Publication Data
US 2019/0336096 A1   Nov. 7, 2019

(51) Int. Cl.
*A61B 6/00* (2006.01)
*G16H 30/40* (2018.01)
*G16H 10/60* (2018.01)
*A61B 6/03* (2006.01)
*A61B 34/10* (2016.01)
(Continued)

(52) U.S. Cl.
CPC .......... *A61B 6/5217* (2013.01); *A61B 5/7267* (2013.01); *A61B 6/032* (2013.01); *A61B 6/504* (2013.01); *A61B 6/507* (2013.01); *A61B 34/10* (2016.02); *G06N 20/00* (2019.01); *G16H 10/60* (2018.01); *G16H 30/40* (2018.01); *A61B 2034/105* (2016.02)

(58) Field of Classification Search
CPC . A61B 2034/105; A61B 34/10; A61B 5/0033; A61B 5/02028; A61B 5/7267; A61B 6/032; A61B 6/504; A61B 6/507; A61B 6/5217; G06N 20/00; G16H 10/60; G16H 30/40
See application file for complete search history.

(56) References Cited

U.S. PATENT DOCUMENTS

| | | | |
|---|---|---|---|
| 6,236,878 | B1 | 5/2001 | Taylor et al. |
| 7,860,290 | B2 | 12/2010 | Gulsun et al. |
| 7,953,266 | B2 | 5/2011 | Gulsun et al. |

(Continued)

FOREIGN PATENT DOCUMENTS

WO   WO2016075331 A2   5/2016

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.
(Continued)

*Primary Examiner* — Manuchehr Rahmjoo

(57) ABSTRACT

A method and system for fast non-invasive computer-based computation of a hemodynamic index, such as fractional flow reserve (FFR) from medical image data of a patient is disclosed. A patient-specific anatomical model of one or more arteries of a patient is automatically generated based on medical image data of the patient. Regions in the automatically generated patient-specific anatomical model for which user feedback is required for accurate computation of a hemodynamic index are predicted using one or more trained machine learning models.

23 Claims, 5 Drawing Sheets

(51) Int. Cl.
*A61B 5/00* (2006.01)
*G06N 20/00* (2019.01)

(56) References Cited

U.S. PATENT DOCUMENTS

| | | | |
|---|---|---|---|
| 8,098,918 B2 | 1/2012 | Zheng et al. | |
| 8,157,742 B2 | 4/2012 | Taylor | |
| 8,200,466 B2 | 6/2012 | Spilker et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 8,386,188 B2 | 2/2013 | Taylor et al. | |
| 9,349,178 B1 | 5/2016 | Itu et al. | |
| 9,747,525 B2 | 8/2017 | Sauer et al. | |
| 9,918,690 B2 | 3/2018 | Itu et al. | |
| 10,463,336 B2 * | 11/2019 | Itu | A61B 5/7267 |
| 2010/0017171 A1 | 1/2010 | Spilker et al. | |
| 2010/0067760 A1 | 3/2010 | Zhang et al. | |
| 2011/0224542 A1 | 9/2011 | Mittal et al. | |
| 2012/0022843 A1 | 1/2012 | Ionasec et al. | |
| 2012/0041301 A1 | 2/2012 | Redel | |
| 2012/0041318 A1 | 2/2012 | Taylor | |
| 2012/0041319 A1 | 2/2012 | Taylor et al. | |
| 2012/0041320 A1 | 2/2012 | Taylor | |
| 2012/0041321 A1 | 2/2012 | Taylor et al. | |
| 2012/0041322 A1 | 2/2012 | Taylor et al. | |
| 2012/0041323 A1 | 2/2012 | Taylor et al. | |
| 2012/0041324 A1 | 2/2012 | Taylor et al. | |
| 2012/0041735 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0072190 A1 | 3/2012 | Sharma et al. | |
| 2012/0121151 A1 | 5/2012 | Bernhardt et al. | |
| 2012/0150516 A1 | 6/2012 | Taylor et al. | |
| 2012/0203530 A1 | 8/2012 | Sharma et al. | |
| 2012/0243761 A1 | 9/2012 | Senzig et al. | |
| 2013/0054214 A1 | 2/2013 | Taylor | |
| 2013/0064438 A1 | 3/2013 | Taylor et al. | |
| 2013/0132054 A1 | 5/2013 | Sharma et al. | |
| 2013/0246034 A1 | 9/2013 | Sharma et al. | |
| 2014/0058715 A1 | 2/2014 | Sharma et al. | |
| 2014/0114184 A1 | 4/2014 | Klaiman et al. | |
| 2014/0270427 A1 | 9/2014 | Fonte et al. | |
| 2015/0038860 A1 | 2/2015 | Fonte et al. | |
| 2015/0112182 A1 | 4/2015 | Sharma et al. | |
| 2015/0324962 A1 | 11/2015 | Itu et al. | |
| 2015/0374243 A1 | 12/2015 | Itu et al. | |
| 2016/0166209 A1 | 6/2016 | Itu et al. | |
| 2016/0196384 A1 | 7/2016 | Mansi et al. | |
| 2017/0032097 A1 | 2/2017 | Itu et al. | |
| 2017/0220760 A1 | 8/2017 | Fonte | |
| 2017/0245821 A1 | 8/2017 | Itu et al. | |
| 2017/0258433 A1 * | 9/2017 | Gulsun | G06T 7/11 |
| 2017/0293735 A1 | 10/2017 | Itu et al. | |
| 2017/0329905 A1 | 11/2017 | Passerini et al. | |

OTHER PUBLICATIONS

Chamuleau et al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Artery Flow Velocity is Related to Lumen Area and Regional Left Ventricular Mass," Circulation, vol. 102, pp. 48-54, 2000.

Itu, Lucian et al., "A Parameter Estimation Framework for Patient-Specific Hemodynamic Computations," Journal of Computational Physics, pp. 316-333, Oct. 22, 2014.

Itu et al., "A Machine-Learning Approach for Computation of Fractional Flow Reserve from Coronary Computed Tomography"; J Appl Physiol; Apr. 14, 2016; vol. 121; pp. 42-52.

Extended European Search Report (EESR) dated Sep. 10, 2019 in corresponding European Patent Application No. 19168050.3.

* cited by examiner

SYSTEM AND METHODS FOR FAST COMPUTATION OF COMPUTED TOMOGRAPHY BASED FRACTIONAL FLOW RESERVE

BACKGROUND OF THE INVENTION

The present invention relates generally to non-invasive computation of hemodynamic indices for an arterial stenosis, and more particularly to fast non-invasive computation of hemodynamic indices, such as fractional flow reserve, based on medical image data of a patient.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance of the stenosis and has a number of other limitations. Pressure wire based FFR measurements involve risks associated with the intervention necessary to insert the pressure wire into the vessel, and for a very narrow stenosis, the pressure wire may induce an additional pressure drop.

In recent years, there has been considerable focus on computational approaches for modeling the flow of blood in the human cardiovascular system. Blood flow computations, performed using computational fluid dynamics (CFD) algorithms, when used in conjunction with patient-specific anatomical models extracted from medical images, have been proposed for diagnosis, risk stratification, and surgical planning. However, such computational approaches often require long computation times.

BRIEF SUMMARY OF THE INVENTION

The present invention provides a method and system for fast non-invasive computation of hemodynamic indices based on medical image data of a patient.

In an embodiment, a method for providing fast non-invasive computer-based computation of a hemodynamic index from medical image data of a patient comprises: automatically generating a patient-specific anatomical model of one or more arteries of a patient based on medical image data of the patient; and predicting regions in the automatically generated patient-specific anatomical model for which user feedback is required for accurate computation of a hemodynamic index using one or more trained machine learning models.

In an embodiment, automatically generating a patient-specific anatomical model of one or more arteries of a patient based on medical image data of the patient comprises: automatically extracting centerlines and cross-sectional contours for each of the one or more arteries of the patient from the medical image data of the patient.

In an embodiment, predicting regions in the automatically generated patient-specific anatomical model for which user feedback is required for accurate computation of a hemodynamic index using one or more trained machine learning models comprises: predicting the regions in the automatically generated patient-specific anatomical model for which user feedback is required for accurate computation of the hemodynamic index using the one or more trained machine learning models based on extracted features related to the automatically generated patient-specific anatomical model that are input to the one or more trained machine learning models.

In an embodiment, the features include features extracted from the medical image data of the patient.

In an embodiment, the features include non-invasive patient data and measurements acquired for the patient.

In an embodiment, the features include features extracted from the automatically generated patient-specific anatomical model of the one or more arteries of the patient.

In an embodiment, the method further comprises: automatically computing initial values for the hemodynamic index at a plurality of locations in the automatically generated patient-specific anatomical model of the one or more arteries of the patient, wherein the features include the initial values computed for the hemodynamic index at the plurality of locations in the automatically generated patient-specific anatomical model and features extracted from the initial values for the hemodynamic index at the plurality of locations in the automatically generated patient-specific anatomical model.

In an embodiment, automatically computing initial values for the hemodynamic index at a plurality of locations in the automatically generated patient-specific anatomical model of the one or more arteries of the patient comprises: computing initial values for the hemodynamic index at the plurality of locations in the automatically generated patient specific anatomical model of the one or more arteries using a second trained machine learning model.

In an embodiment, the method further comprises: performing an automated anatomical evaluation of the one or more arteries of the patient in the automatically generated patient-specific anatomical model, wherein the features include anatomical features related to one or more stenosis regions in the one or more arteries of the patient extracted from results of the automated anatomical evaluation of the one or more arteries of the patient in the automatically generated patient-specific anatomical model.

In an embodiment, the method further comprises: requesting user feedback for only the regions in the automatically generated patient-specific anatomical model predicted by the one or more trained machine learning models as requiring user feedback for accurate computation of the hemodynamic index; receiving user feedback for the regions in the automatically generated patient-specific anatomical model predicted by the one or more trained machine learning models as requiring user feedback for accurate computation of the hemodynamic index, resulting in a revised anatomical model of the one or more arteries of the patient; and computing final values for the hemodynamic index at a plurality of locations in the one or more arteries of the patient based on the revised anatomical model of the one or more arteries of the patient.

In an embodiment, the one or more trained machine learning models include a first trained machine learning model for predicting user feedback requirements at a tree level, a second trained machine learning model for predicting user feedback requirements at a branch level, and a third trained machine learning model for predicting user feedback requirements at a cross-sectional contour level.

In an embodiment, the hemodynamic index is fractional flow reserve.

In an embodiment, the one or more arteries of the patient comprise one or more coronary arteries of the patient.

In an embodiment, an apparatus for providing fast non-invasive computation of a hemodynamic index from medical image data of a patient, comprises: a processor and a memory storing computer program instructions which when executed by the processor cause the processor to perform operations comprising: automatically generating a patient-specific anatomical model of one or more arteries of a patient based on medical image data of the patient; and predicting regions in the automatically generated patient-specific anatomical model for which user feedback is required for accurate computation of a hemodynamic index using one or more trained machine learning models.

In an embodiment, a non-transitory computer readable medium stores computer program instructions for providing fast non-invasive computation of a hemodynamic index from medical image data of a patient, the computer program instructions when executed by a processor cause the processor to perform operations comprising: automatically generating a patient-specific anatomical model of one or more arteries of a patient based on medical image data of the patient; and predicting regions in the automatically generated patient-specific anatomical model for which user feedback is required for accurate computation of a hemodynamic index using one or more trained machine learning models.

These and other advantages of the invention will be apparent to those of ordinary skill in the art by reference to the following detailed description and the accompanying drawings.

DETAILED DESCRIPTION

Figure 1:
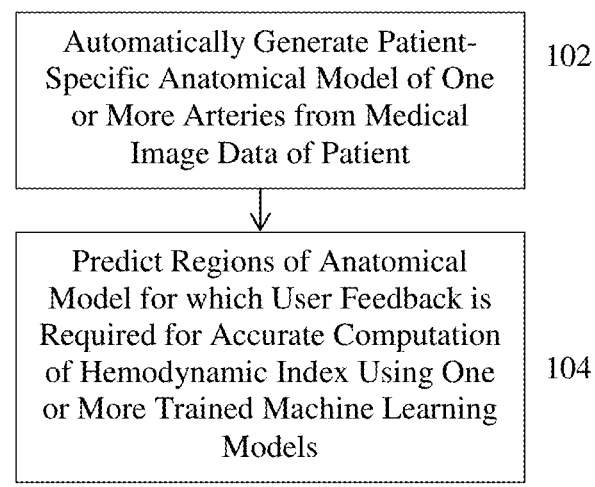
FIG. 1 illustrates a method for predicting where user feedback is required in an anatomical model to provide fast computer-based computation of a hemodynamic index from medical image data according to an embodiment of the present invention.

The present invention provides a method and system for fast non-invasive computation of hemodynamic indices based on medical image data of a patient. Embodiments of the present invention are described herein to give a visual understanding of methods for fast computer-based computation of hemodynamic indices, such as fractional flow reserve (FFR), from medical image data, such as computed tomography angiography (CTA) images, of a patient. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

In recent years, there has been considerable focus on using computational approaches for modeling the flow of blood in the human cardiovascular system to perform non-invasive medical image-based assessment of arterial stenosis. In such computational approaches, blood flow computations, performed using computational fluid dynamics (CFD) algorithms, are used in conjunction with patient-specific anatomical models extracted from medical images to estimate hemodynamic indices, such as FFR. We have recently introduced a machine learning (ML) model for FFR computation as an alternative to CFD-based modeling for non-invasive hemodynamic assessment of arterial stenoses. For example, the machine learning model for FFR computation is described in Itu et al., "A Machine Learning Approach for Computation of Fractional Flow Reserve from Coronary Computed Tomography," *Journal of Applied Physiology*, Volume 121, 2016, pp. 42-52, which is incorporated herein in its entirety by reference. We have shown that such the performance of machine learning model is not statistically discernable from that of the CFD approach. In addition, the computation time for computing FFR using the machine learning model is much faster than that of the CFD approach.

Given an anatomical model (i.e., lumen segmentation) of the patient's coronary arteries (or other arteries), the computer-based computation of FFR using the machine learning model (cFFRML) is fully automatic, without requiring user intervention. However, in existing methods, the pre-processing pipeline to generate the anatomical is only semi-automatic. The system (computer) presents the user (e.g., clinician) with automatically extracted centerlines and cross-sectional contours, which can then be interactively edited by the user to create the anatomical model. For example, editing may be required in atherosclerotic regions where the automatically performed segmentation has a lower accuracy and confidence, and which also have the highest influence on the computed FFR values. Since, in existing computer-based techniques for non-invasive hemodynamic assessment, there is no method for automatically determining a priori the regions where user interaction/editing is crucial for obtaining accurate FFR estimation results and regions where user editing will have little influence on the FFR estimation results, the main bottleneck in terms of the overall processing time remains the preparation of the anatomical model/extraction of the anatomical information required for computing the FFR.

Different approaches are currently used in preparation of the anatomical model in existing computer-based techniques for non-invasive computation of hemodynamic indices. In a thorough approach, the user needs to review all of the branches and all cross-sections before FFR can be computed. This leads to large processing times. In another approach, the user is allowed to focus on locations which he/she believes to be crucial for the accuracy of the finally computed FFR values (e.g., stenotic regions). The disadvantage of this approach is that is it subjective, leading to high intra- and inter-user variability. In addition, this approach may lead to inaccurate final computed FFR values if the user chooses to ignore a region that has a high influence on the final FFR values.

Embodiments of the present invention provide an improvement to existing methods for computer-based non-invasive computation of hemodynamic indices, such as FFR, that ensures fast and accurate computation of medical image (e.g., CT) based hemodynamic indices. Embodiments of the present invention reduce to a minimum the user interaction during the preparation of the anatomical model, while preserving accuracy of the final computed FFR values. In an embodiment of the present invention, the starting point is an automatically generated anatomical model of one or more arteries of the patient that is generated from medical image data of the patient, such as CAT images. For example, the automatically generated anatomical model may include centerlines and cross-section contours of the one or more arteries. The user interaction typically refers to correcting the vessel centerlines, for example to add new branches or remove branches (e.g., veins identified as arteries), and correcting the cross-section contours (this occupies the most time). Embodiments of the present invention utilize one or more machine learning models to indicate/predict certain parts of the arterial geometry where user feedback is required for obtaining accurate computed FFR (cFFR) results, while for the remaining parts, the automatically extracted information is used without requesting any feedback from the user. This provides an improvement over existing computer-based methods by reducing the time required for user editing and thus reducing the total computation time for the computer-based computation of FFR (or other hemodynamic indices), while preserving accurate FFR computations. In addition, the method described herein provides an advantage over existing computer-based methods in reducing intra- and inter-user variability of cFFR results.

FIG. 1 illustrates a method for predicting where user feedback is required in an anatomical model to provide fast computer-based computation of a hemodynamic index from medical image data according to an embodiment of the present invention. In an advantageous embodiment, the hemodynamic metric is FFR, but the present invention is not limited thereto. In other embodiments, other hemodynamic indices may be computed, such as instantaneous wave-free ratio (iFR), rest distal-to-aortic pressure ratio (Pd/Pa), computational flow reserve (CFR), hyperaemic stenosis resistance (HSR), baseline stenosis resistance (BSR), index of microvascular resistance (IMR), or wall shear stress. As illustrated in FIG. 1, at step 102, a patient-specific anatomical model of one or more arteries of the patient is automatically generated from medical image data of the patient. In an advantageous embodiment, the arteries are coronary arteries and the medical image data is one or more coronary computed tomography angiography (CCTA) images of the patient. At step 104, one or more trained machine learning models are used to predict regions of the patient-specific anatomical model for which user feedback is required for accurate computation of the hemodynamic index. In a possible implementation, regions at different resolutions may be targeted by different trained machine learning models. For example, trained machine learning models may make predictions at a tree level (collection of branches), branch level, and/or cross-sectional level. In any of the embodiments described herein, which are used to determine regions of an arterial tree where user feedback is required and regions in which no user feedback is required, all or some of the regions in which no user feedback is required may be discarded at the time of cFFR computation. The method steps in FIG. 1 are described in greater detail below in connection with the more detailed method illustrated in FIG. 2.

Figure 2:
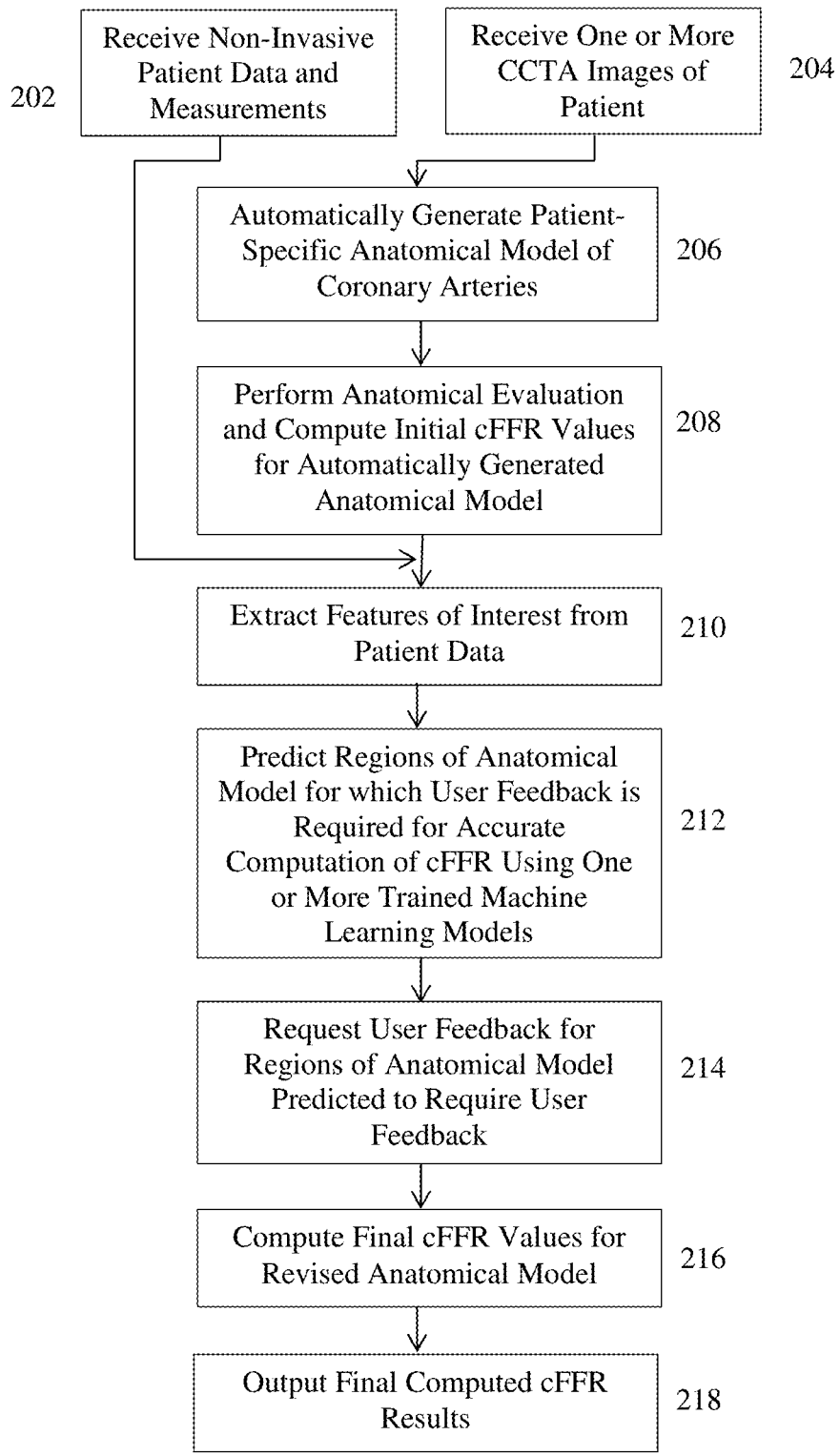
FIG. 2 illustrates a method for fast non-invasive computation of fractional flow reserve (FFR) in coronary arteries of a patient based on coronary computed tomography angiography (CCTA) data according to an embodiment of the present invention.

FIG. 2 illustrates a method for fast non-invasive computation of fractional flow reserve (FFR) in coronary arteries of a patient based on coronary computed tomography angiography (CCTA) data according to an embodiment of the present invention. The method of FIG. 2 provides an improvement to existing computer-based methods for non-invasive computation of FFR. Although the embodiment of FIG. 2 describes fast computation of FFR for coronary arteries from CCTA data, the method may be similarly applied for computation of other hemodynamic indices (e.g., iFR, rest Pd/Pa, CFR, HSR, BSR, IMR, wall shear stress, etc.). Further, the method of FIG. 2 may be similarly applied for fast non-invasive computation FFR or other hemodynamic indices in other types of arteries from medical images (e.g., CTA) of such arteries.

Referring to FIG. 2, at step 202, non-invasive patient data and measurements of the patient are received. The non-invasive patient data and measurements may include demographic data, patient history, non-invasive measurements acquired using medical equipment and devices, such as stethoscope, blood pressure meter, and non-medical grade devices (e.g., wearables), laboratory diagnostics, and measurements from non-invasive tests (e.g., myocardial perfusion imaging (MPI), stress echo, etc.). For example, measurements such as blood pressure, heart rate, ECG can be acquired using non-invasive medical devices. Results of previously performed non-invasive stress tests, such as MPI, multigated acquisition (MUGA) scan, radionuclide stress test and nuclear stress test, exercise stress test, electrocardiogram (EKG/ECG), stress/rest electrocardiography. In a possible embodiment, demographics information and medical history may include age, ethnicity, gender, weight, height, race, body mass index (BMI), diabetes, hypertension, hypercholesterolemia, smoking history, family history of CAD, prior myocardial infarction (MI), prior percutaneous coronary intervention (PCI), prior coronary artery bypass grafting (CABG), angina type (stable, worsening, silent ischemia, or other angina category according to Canadian Cardiovascular Society (CCS) or American Heart Association (AHA)/American College of Cardiology (ACC)). The non-invasive patient data and measurements can be received by inputting newly acquired data and measurements and/or by retrieving previously stored data and measurements.

At step 204, one or more CCTA images of the patient are received. In an advantageous embodiment, one or more 3D CCTA images are received. The CCTA images may be received directly from an image acquisition device (CT scanner) or may be received by loading previously stored CCTA images for a patient.

At step 206, a patient-specific anatomical model of the coronary arteries is automatically generated from the one or more CCTA images of the patient. The patient-specific anatomical model can be generated by segmenting the coronary arteries in the CCTA image data using an automated coronary artery centerline extraction algorithm. For example, the coronary arteries can be segmented in a CT volume using the method described United States Published Patent Application No. 2010/0067760, entitled "Method and System for Automatic Coronary Artery Detection," the disclosure of which is incorporated herein by reference in its entirety. Once a coronary artery centerline tree is extracted, cross-section contours can be generated at each point of the centerline tree. The cross-section contour at each centerline point gives a corresponding cross-section area measurement at that point in the coronary artery. Other segmentation methods may also be employed. In one embodiment, the patient-specific anatomical model includes the extracted centerlines and cross-section contours. In another possible embodiment, the patient-specific anatomical model can be a 3D mesh generated from the centerlines and cross-section contours. In this case, a 3D anatomical surface model is generated for the segmented coronary arteries. For example, methods for anatomical modeling of the coronary arteries are described in U.S. Pat. No. 7,860,290, entitled "Three-Dimensional (3D) Modeling of Coronary Arteries," and U.S. Pat. No. 7,953,266, entitled "Robust Vessel Tree Modeling," the disclosures of which are incorporated herein by reference in their entirety. In addition to the coronaries, the patient-specific anatomical model can include the aortic root together with the proximal part of the aorta.

At step 208, an anatomical evaluation of the coronary arteries is performed and initial cFFR values are computed at locations in the automatically generated anatomical model of the coronary arteries. The anatomical evaluation of the coronary arteries is performed using an automated method or model that automatically locates stenosis regions in the coronary arteries and then automatically performs an anatomical evaluation of each detected stenosis region. Stenosis regions may be automatically detected in the image data using an algorithm for automatic detection of coronary artery stenosis, such as the method for automatic detection of coronary artery stenosis described in United States Published Patent Application No. 2011/0224542, entitled "Method and System for Automatic Detection and Classification of Coronary Stenoses in Cardiac CT Volumes," the disclosure of which is incorporated herein by reference in its entirety. An automated anatomical evaluation algorithm may then be applied to each stenosis region to determine information such as stenosis grade, stenosis length, and plaque characteristics (e.g., composition (fatty, fibrous, calcified), size, high risk plaque characteristics, degree of positive remodeling) for each stenosis region. For example, such anatomical evaluation is described in U.S. Pat. No. 9,349,178, entitled "Synthetic Data-Driven Hemodynamic Determination in Medical Imaging," the disclosure of which is incorporated herein by reference in its entirety.

In an advantageous embodiment, initial cFFR values at various locations in the automatically generated anatomical model of the coronary arteries are computed using a trained machine learning model. In this case, geometric features may be extracted from or the automatically generated anatomical model and input to a trained machine learning model that computed the cFFR values based on the input features. For example, such machine learning based computation of cFFR values for an anatomical model of the coronary arteries is described in Itu et al., "A Machine Learning Approach for Computation of Fractional Flow Reserve from Coronary Computed Tomography," *Journal of Applied Physiology*, Volume 121, 2016, pp. 42-52, U.S. Pat. No. 9,538,925, entitled "Method and System for Machine Learning Based Assessment of Fractional Flow Reserve," U.S. Pat. No. 9,349,178, entitled "Synthetic Data-Driven Hemodynamic Determination in Medical Imaging," and United States Publication No. 2017/0245821, entitled "Method and System for Purely Geometric Machine Learning Based Fractional Flow Reserve," the disclosures of which are incorporated herein by reference in their entirety.

At step 210, features of interest are extracted from the patient data. The features can be extracted from the non-invasive patient data and measurements, the CCTA image data, the automatically generated patient-specific anatomical model, the results of the anatomical evaluation of the coronary arteries, and the initial cFFR values computed for the automatically generated anatomical model. The extracted features of interest are input to one or more trained machine learning models, which are used (in step 212) to predict regions of the automatically generated anatomical model that require user interaction for accurate cFFR computation. The trained machine learning model acts as a decision support system, which uses as input the extracted features. The features to the trained machine learning model may include any of the following:

The CCTA imaging data;
The automatically generated anatomical model, including but not limited to centerlines, automatic or user-edited (when these steps are repeated) lumen segmentation, probability maps of lumen location, coronary mask, etc., as well as confidence metrics calculated at each location of the coronary tree;
The results of the anatomical evaluation of the coronary arteries, such as stenosis grades, stenosis lengths, stenosis locations, and plaque characteristics such as composition (fatty/fibrous/calcified), size, high risk characteristics, and degree of positive remodeling. In addition, any of the anatomical features described in U.S. Pat. No. 9,349,178, entitled "Synthetic Data-Driven Hemodynamic Determination in Medical Imaging," which is incorporated herein by reference in its entirety, may be extracted as input to the trained machine learning model;
Other metrics derived from the CCTA image data: image quality, calcium score, transluminal attenuation gradient (TAG), risk scores (e.g., segment stenosis risk score, segment involvement score, Framingham risk score, etc.);
The initial cFFR values computed based on the automatically generated anatomical model, as well as metrics of uncertainty (e.g., standard deviation, confidence intervals, probability density functions, etc.);
Local sensitivity values at each location of the coronary anatomical model (i.e., how sensitive is the initial computed cFFR value with respect to the variation of the cross-sectional area at each location);
Other medical equipment and device measurements: stethoscope, blood pressure meter, laboratory diagnostics, etc. (blood pressure, heart rate, ECG signals);
Type of patient: stable or acute;
Results of previously performed non-invasive stress tests: MPI, MUGA scan, radionuclide stress test and nuclear stress test, exercise stress test, electrocardiogram (EKG/ECG), and/or stress/rest echocardiography;
Demographics information (e.g., age, ethnicity, gender, weight, height, race, BMI, diabetes, hypertension, hypercholesterolemia, smoking history, family history of CAD, prior MI, prior CABG, angina type (stable/worsening/silent ischemia/other angina type according to CCS or AHA/ACC)); and
Clinical history of the patient, e.g., if medical images of the coronary arteries have been acquired before, this information can be used to estimate which regions of the coronary circulation are pathologic.

All of the different input information/features may be acquired at a single time point, or at different time points. For example, features extracted from a previous CCTA or from other previously performed imaging tests may be input to the machine learning model to predict the regions that require user interaction.

At step 212, one or more trained machine learning models are used to predict regions of the automatically generated anatomical model that require user interaction for accurate cFFR computation based on the input features. The features extracted in step 210 are input to one or more trained machine learning models, and the trained machine learning models predict on a region-by-region basis whether user feedback to the automatically generated anatomical model is required for accurate computation of cFFR.

The trained machine learning models are trained in an offline training stage to make decisions as to whether user feedback is required for regions in the automatically generated anatomical model of the coronary arteries based on the various features input to the trained machine learning models. Examples of the types of decisions that may be taken by the trained machine learning models based on the above described types of input features as a result of the training include: not asking for user feedback in regions where the confidence of the automatically generated anatomical model is high; not asking for user feedback in regions where the local sensitivity to cFFR is low; asking for user feedback in regions where no stenosis is present but positive remodeling can be observed (i.e., plaque is present); not asking for user feedback when the image quality is high and/or the calcium score is low; not asking for user feedback is regions where the cFFR value is high even for a low threshold of the associated confidence interval; not asking for user feedback in a certain region of the coronary tree where a perfusion indicated normal coronary perfusion; and asking for user feedback is a region where a previous imaging exam identified atherosclerosis. It is to be understood that such decisions are exemplary and the present invention is not limited thereto, and the decisions/predictions by the trained machine learning models are made from the set features input and are learned from the training of the machine learning models based on a database of training samples. The training of the machine learning models is described in greater detail below in connection with FIG. 4.

The one or more trained machine learning models can include multiple machine learning models that are used in a cascaded or parallel workflow. In an advantageous embodiment, the one or more trained machine learning models can include a plurality of trained machine learning classifiers each trained to classify regions of the automatically generated anatomical model at a different resolution or level of granularity. For example, a first trained machine learning model may be used to classify each of the coronary arteries in the automatically generated anatomical model at a tree level, a second trained machine learning model may be used to classify individual branches at a branch level, and a third trained machine learning model may classify point by point within a branch or segment at a cross-sectional contour level. These machine learning models can be applied in a cascaded workflow such that the first trained machine learning model is first applied to each coronary artery in the automatically generated anatomical model to predict whether any user feedback is required for that coronary artery tree. If the first trained machine learning model predicts that user feedback is required for a particular coronary artery tree, the second trained machine learning model is applied to evaluate each branch in the coronary artery tree to predict whether any user feedback is required for that branch. If the second trained machine learning model predicts that user feedback is required for a particular branch, the third trained machine learning model is then applied on a point-by-point basis along the branch to predict which cross-section contours require user feedback.

In another possible embodiment, the one or more trained machine learning models can include different machine learning models trained to evaluate different arteries in the automatically generated anatomical model. For example different trained machine learning models used to predict which regions require user feedback in the right coronary artery, the left main coronary artery, the left anterior descending coronary artery. In this case, the different machine learning models trained for the different coronary arteries can be applied in parallel.

In advantageous embodiments of the present invention, deep learning based methods may be used to train each machine learning model. Deep learning refers to a category of artificial intelligence techniques in which a machine learning model includes multiple information processing layers for which weights are learned during training. In such deep learning based machine learning models, hierarchical structures are employed, either for learning the features for representation of the patient data (during training) or for classification or regression during the online prediction stage. Various deep learning architectures can be used for the machine learning models. In an exemplary implementation, each of the one or more trained machine learning models can be implemented as a convolutional neural network (CNN). The CNN can take as input both imaging and non-imaging features and provide decisions/predictions (e.g., user feedback is required/not required) for different parts of the coronary tree or different parts of the image. The CNN may be implemented as a multi-task CNN that also provides as output confidence measures for the output predictions. In another exemplary implementation, each of the one or more machine learning models can be implemented using a long short term memory (LSTM) network. In this implementation, segments of the coronary anatomical model are fed to the network sequentially (e.g., starting from the root of the coronary tree). The LSTM model is then able to output a decision/prediction for each segment and may use the information from previous segments to make the prediction at the current segment. In either implementation, the deep learning architecture may be trained as a classification model with binary or multi-class outputs or as a regression model with continuous outputs.

In one embodiment, the measure of interest to be predicted by the machine learning model may be a binary value indicating a classification of a given location or region as requiring user feedback or not requiring user feedback. For example, a value of 1 may be output for a region or location requiring user feedback for accurate computation of cFFR and a value of 0 may be output for a region or location not requiring user feedback for accurate computation of cFFR. In another embodiment, the machine learning model may provide continuous output values. For example, the machine learning model may output a probability score between 0 and 1 for a given location or region, indicating a predicted probability that user feedback is required for that location or region. The predicted probability score for a given region/location is then compared to a threshold, and the region/location in the automatically generated anatomical model is determined to require user feedback if the predicted probability value is greater than the threshold. According to an exemplary implementation, different threshold values may be employed from case to case to determine which regions require user feedback and which regions can be used as given by the automatically generated anatomical model. For example, the threshold value may be higher in cases of acute patients where a decision needs to be taken fast, and lower for stable coronary artery disease (CAD) patients where delaying the decision poses no risk to the patient. The threshold value itself may be determined automatically by another machine learning algorithm for each case. The threshold value may be additionally be based on a cost analysis, in which case the decision to ask for user feedback may be based at least in part on cost-effectiveness. In another possible implementation, one or more predetermined threshold values can be applied.

Figure 3:
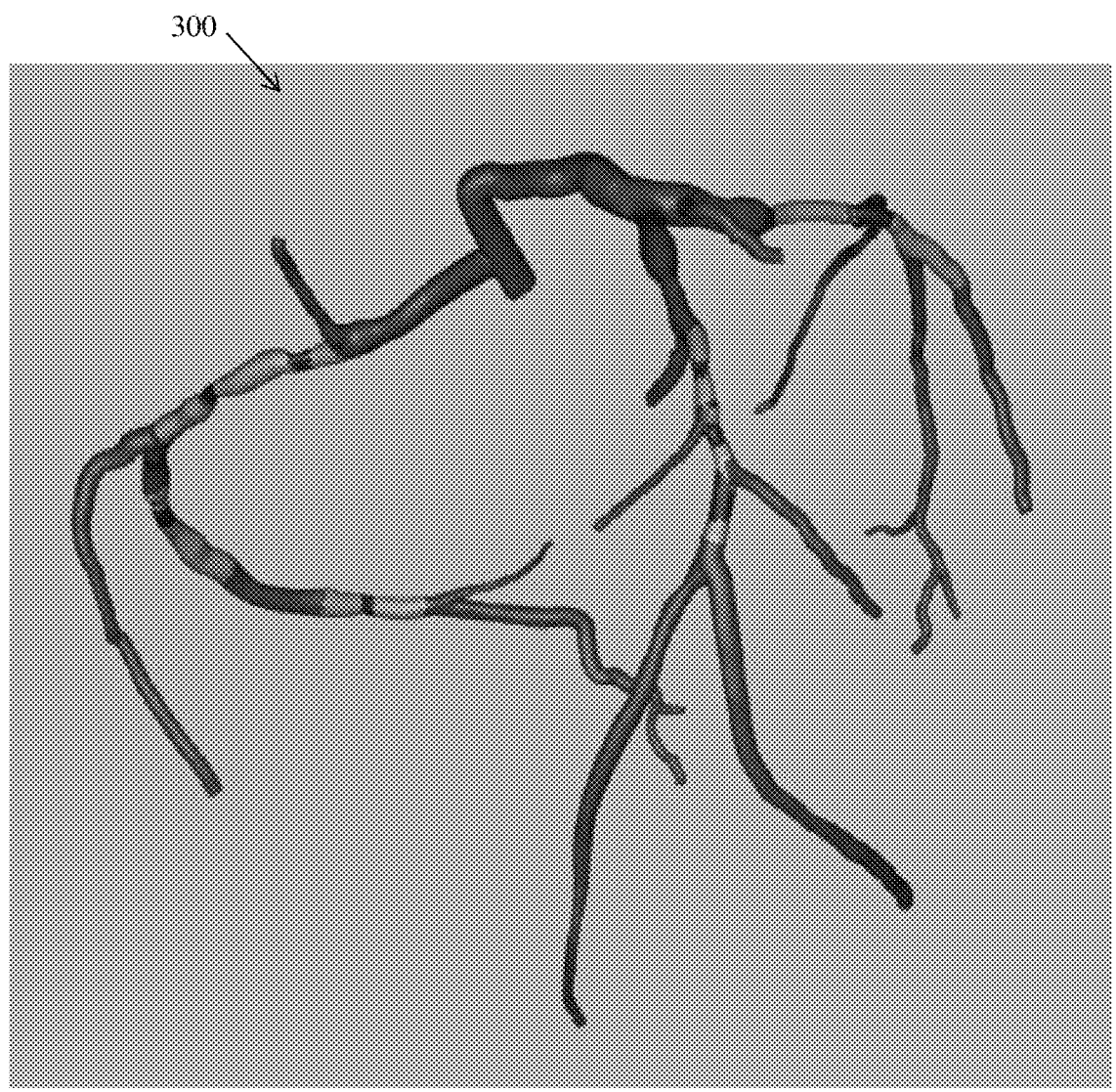
FIG. 3 illustrates an exemplary output map of a machine learning model.

The trained machine learning model(s) can output a map of the automatically generated anatomical model of the coronary arteries that shows the predictions of which regions require user feedback and which regions do not require user feedback. For example, the machine learning model can output a color coded probability map of the anatomical model in which different colors represent different predicted probabilities for requiring user feedback. Alternatively, the machine learning model can output a binary map that shows the regions predicted to require user feedback. Such maps can be displayed on a display device of a computer system. FIG. 3 illustrates an exemplary output map 300 of a machine learning model. As shown in FIG. 3, the output map 300 is a color coded map of the automatically generated anatomical model of the coronary arteries with different colors represented different probability scores output by the trained machine learning model.

Returning to FIG. 2, at step 214, user feedback is requested for the regions of the automatically generated anatomical model predicted to require user feedback. In one embodiment, an output map showing the predicted regions that require user feedback can be displayed on a display device. An example of such an output map 300 is shown in FIG. 3. The user can then select each region that is predicted to require user feedback and edit that region of the automatically generated anatomical model to correct the cross-sectional contours in that region. For example, the user can use an input device (e.g., mouse, touchscreen, etc.) to edit the automatically generated anatomical model. In another embodiment, an iterative process can be used to sequentially display to the user only the regions predicted to require user feedback and request user input for each sequentially displayed region.

In a possible embodiment, the user feedback predictions for the anatomical model may be updated in real time while the user is providing feedback. Corrections at proximal locations in an artery may effect the predictions regarding whether user feedback is required at distal locations in the artery. In this embodiment, the regions predicted to require user feedback are shown to the user in order from proximal to distal with respect to the blood flow direction. When user feedback to correct the cross-sectional contours for a particular region is received, steps 208-212 of the method of FIG. 2 are repeated with the updated anatomical model to obtain updated predictions for whether the regions/locations distal to the corrected region require user feedback. For example, while the user is correcting cross-sectional contours in the proximal left anterior descending (LAD) artery, the predictions as to whether feedback is required in the distal LAD may be re-evaluated in real time, possibly leading to the updated prediction that feedback is no longer required (e.g., cFFR in the distal LAD is high with a high confidence). Real time updates of the predictions are feasible because both the machine learning models for computing cFFR and associated confidence intervals and the machine learning models for predicting the user feedback requirements provide results in real time and can be applied iteratively when the user is providing feedback for certain regions of the anatomical model. In an exemplary implementation, the machine learning models may be employed to make predictions based on partial information, such as anatomical information extracted using fully automated centerline and segmentation algorithms, anatomical information of the main branches, a subset of the features that are used for the CT-cFFR machine learning model that can be determined automatically or with limited user interaction, and measures of uncertainty for any type of the above listed features and information.

At step 216, final cFFR values are determined for the revised anatomical model. The user feedback to edit the anatomical model results in a revised patient-specific anatomical model of the coronary arteries. In an advantageous embodiment, final cFFR values can be computed at locations in the revised anatomical model using a trained machine learning model for FFR computation. Such machine learning based computation of cFFR values for an anatomical model of the coronary arteries is described in Itu et al., "A Machine Learning Approach for Computation of Fractional Flow Reserve from Coronary Computed Tomography," Journal of Applied Physiology, Volume 121, 2016, pp. 42-52, U.S. Pat. No. 9,538,925, entitled "Method and System for Machine Learning Based Assessment of Fractional Flow Reserve," U.S. Pat. No. 9,349,178, entitled "Synthetic Data-Driven Hemodynamic Determination in Medical Imaging," and United States Publication No. 2017/0245821, entitled "Method and System for Purely Geometric Machine Learning Based Fractional Flow Reserve," the disclosures of which are incorporated herein by reference in their entirety. In an alternative embodiment, CFD based simulations can be used to simulate blood flow and pressure in the revised anatomical model of the coronary arteries and the final cFFR values can be computed based on the CFD based simulations.

In one embodiment, certain parts of the coronary anatomy may be discarded completely while computing the final cFFR values. In this case, the initial cFFR values can be used for such parts of the coronary artery and no further computation of cFFR values is needed for these parts. For example, if the right coronary artery (RCA) tree is considered to be completely healthy (based on the generated anatomical information, plaque information, etc.), no further computations may be performed for the RCA.

In another embodiment, small side branches may be discarded for the cFFR computation. In this case, discarding does not necessarily refer to completely ignoring the information, but instead the corresponding information is used in a different simplified approach. For example, each small side branch may be represented by a bifurcation location and a corresponding healthy radius value. The flow loss in the main branch due to the side branch is estimated and taken into account for model predictions at all downstream locations.

In another embodiment, distal parts of the main branches with small radius values may be discarded from the cFFR computation. Fully automated algorithms may be employed to determine cutting points for each branch, thus discarding locations on each branch.

In U.S. Pat. No. 9,349,178, entitled "Synthetic Data-Driven Hemodynamic Determination in Medical Imaging," an advanced feature called ischemic weight is introduced. Ischemic weight is estimated at the branch level and can be computed either from radius information or from left ventricle (LV) mass information. In another embodiment, if the ischemic weight determined from radius information and from LV mass information is similar, cFFR may be computed on a partial tree using, for example, the machine learning algorithm which is employed for anigoFFR (FFR computed from X-ray angiography medical images) and which has been specifically designed to provide computed FFR values with reduced anatomical information, as described in U.S. Pat. No. 9,349,178, entitled "Synthetic Data-Driven Hemodynamic Determination in Medical Imaging," the disclosure of which is incorporated herein by reference in its entirety.

At step 218, the final cFFR results are output. The final cFFR results can be output by displaying the final cFFR results on a display device of a computer system. In one embodiment, the final cFFR results can be displayed using a color coded map of the revised anatomical model of the coronary arteries in which different colors represent different ranges of cFFR values.

Figure 4:
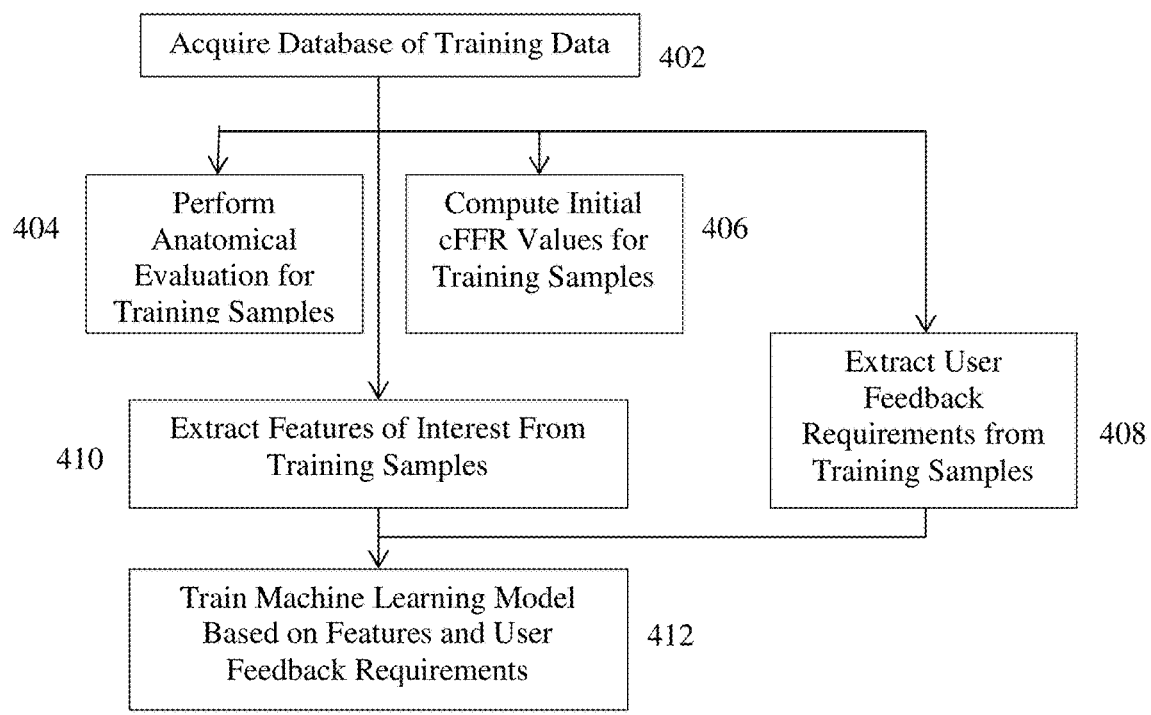
FIG. 4 illustrates a method for training a machine learning model for predicting regions of an arterial anatomical model that require user feedback according to an embodiment of the present invention.

The methods of FIG. 1 and FIG. 2 are used for the prediction phase which is performed online. To be able to use one or more machine learning models for the prediction of user feedback requirements, these machine learning models must be trained a priori offline. FIG. 4 illustrates a method for training a machine learning model for predicting regions of an arterial anatomical model that requires user feedback according to an embodiment of the present invention. Referring to FIG. 4, at step 402, a database of training data is acquired. In one embodiment, a large database containing patient-specific data (for many different patients) is used for training. The database can include medical image data (e.g., CCTA) and non-invasive patient data and measurements (e.g., demographics, patient history, measurements from non-invasive medical devices, such as stethoscope, blood pressure meter, non-medical grade devices, etc.) for each patient, as well as information regarding the automatically generated anatomical model (centerlines and cross-sectional contours), the corrections performed by the user and the associated final cFFR values. At step 404, an automated anatomical evaluation of the coronary arteries is performed for each training sample in the database. At step 406, initial cFFR values are computed for each training sample in the database. Steps 404 and 406 can be performed as described above in connection with step 208 of FIG. 2.

At step 408, user feedback requirements are extracted for each training sample in the database. The database is processed to determine case-by-case which of the corrections performed by the user have influenced the final cFFR values (as compared with the initial cFFR values), thus labeling each correction as required or not required. These labels of required or not required provide ground truth outputs for training the machine learning model. Alternatively, if information on the user performed corrections is not available, the automatically generated anatomical model may be used as a starting point and random corrections may be automatically performed, while observing the variations in the final cFFR values. Thus, labels may be generated automatically for each region.

At step 410, features of interest are extracted from the training samples. Such features of interest are described above in the method of FIG. 2. At step 412, the machine learning model is trained based on the features and the user feedback requirements extracted for the training samples. The machine learning model is a data-driven surrogate model trained using a machine learning algorithm. The machine learning model can be trained to minimize a cost function that represents an error between the ground truth extracted user feedback requirements and the predicted user feedback requirements over the set of training samples.

In advantageous embodiments of the present invention, deep learning based methods may be used to train the machine learning model. Deep learning refers to a category of artificial intelligence techniques in which a machine learning model includes multiple information processing layers for which weights are learned during training. In such deep learning based machine learning models, hierarchical structures are employed, either for learning the features for representation of the patient data (during training) or for classification or regression during the online prediction stage. Various deep learning architectures can be used for the machine learning model. In an exemplary implementation, the machine learning models can be implemented as a convolutional neural network (CNN). The CNN can take as input both imaging and non-imaging features and provide decisions/predictions (e.g., user feedback is required/not required) for different parts of the coronary tree or different parts of the image. The CNN may be implemented as a multi-task CNN that also provides as output confidence measures for the output predictions. In another exemplary implementation, the machine learning model can be implemented using a long short term memory (LSTM) network. In this implementation, segments of the coronary anatomical model are fed to the network sequentially (e.g., starting from the root of the coronary tree). The LSTM model is then able to output a decision/prediction for each segment and may use the information from previous segments to make the prediction at the current segment. In either implementation, the deep learning architecture may be trained as a classification model with binary or multi-class outputs or as a regression model with continuous outputs.

Once the machine learning model is trained, the machine learning model can be stored in a memory or storage of a computer system and used in the prediction phase to perform prediction of user feedback requirements for an automatically generated anatomical model of one or more arteries for a new patient. During the training phase, more features may be available than during the online prediction phase. In an exemplary implementation, the features that are missing during the prediction phase may be estimated based on similar datasets in the training database. For example, a separate machine learning algorithm can be specifically trained for this purpose and employed to estimate the missing features.

In one embodiment, the database used for training the one or more machine learning models may contain only synthetically generated data. Automated methods are employed to generate synthetic CCTA images and synthetic anatomical models including plaque data. For example, various techniques for generating synthetic training data are described in U.S. Pat. No. 9,538,925, entitled "Method and System for Machine Learning Based Assessment of Fractional Flow Reserve," U.S. Pat. No. 9,349,178, entitled "Synthetic Data-Driven Hemodynamic Determination in Medical Imaging," and United States Publication No. 2017/0245821, entitled "Method and System for Purely Geometric Machine Learning Based Fractional Flow Reserve," the disclosures of which are incorporated herein by reference in their entirety. In a possible implementation, a generative adversarial network (GAN) can be used to train a machine learning model to generate synthetic CCTA images. Random corrections in the synthetically generated anatomical models are then performed, while observing the variations in the final cFFR values. Thus, labels are generated automatically on a region-by-region basis. In an exemplary implementation, the type of corrections performed for each region may be learned from previous experience, e.g. based on a database containing patient-specific data and corresponding corrections performed by the user.

Figure 5:
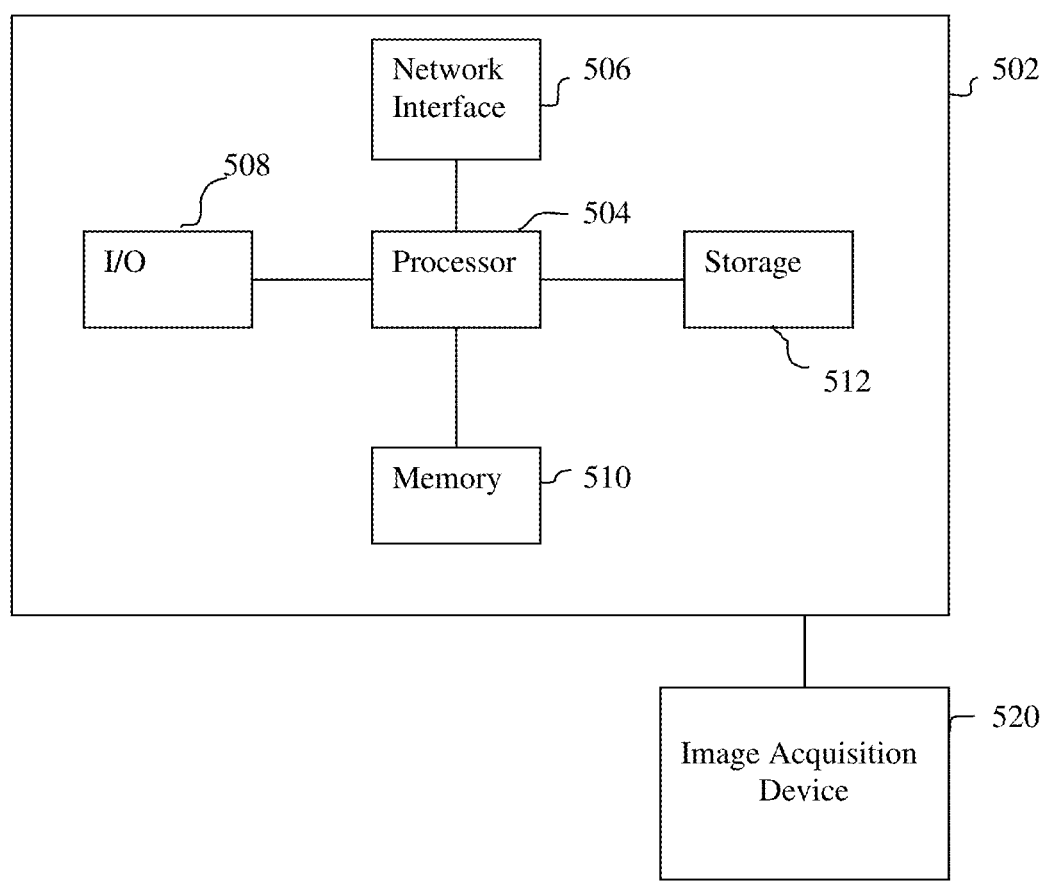
FIG. 5 is a high-level block diagram of a computer capable of implementing the present invention.

The above-described methods may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIGS. 1, 2, and 4 may be defined by the computer program instructions stored in the memory 510 and/or storage 512 and controlled by the processor 504 executing the computer program instructions. An image acquisition device 520, such as a CT scanning device, can be connected to the computer 502 to input image data to the computer 502. The image acquisition device 520 and the computer 502 may communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). One skilled in the art will recognize that an implementation of an actual computer could contain other components as well, and that FIG. 5 is a high level representation of some of the components of such a computer for illustrative purposes.

The above-described methods may be implemented using computers operating in a client-server relationship. Typically, in such a system, the client computers are located remotely from the server computer and interact via a network. The client-server relationship may be defined and controlled by computer programs running on the respective client and server computers.

The above-described methods may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1, 2, and 4. Certain steps of the methods described herein, including one or more of the steps of FIGS. 1, 2, and 4 may be performed by a server or by another processor in a network-based cloud-computing system. Certain steps of the methods described herein, including one or more of the steps of FIGS. 1, 2, and 4, may be performed by a client computer in a network-based cloud computing system. The steps of the methods described herein, including one or more of the steps of FIGS. 1, 2, and 4, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for providing fast non-invasive computer-based computation of a hemodynamic index from medical image data of a patient, comprising:
   automatically generating a patient-specific anatomical model of one or more arteries of a patient based on medical image data of the patient; and
   predicting regions in the automatically generated patient-specific anatomical model for which user feedback is required for accurate computation of a hemodynamic index using one or more trained machine learning models.

2. The method of claim 1, wherein automatically generating a patient-specific anatomical model of one or more arteries of a patient based on medical image data of the patient comprises:
   automatically extracting centerlines and cross-sectional contours for each of the one or more arteries of the patient from the medical image data of the patient.

3. The method of claim 1, wherein predicting regions in the automatically generated patient-specific anatomical model for which user feedback is required for accurate computation of a hemodynamic index using one or more trained machine learning models comprises:
   predicting the regions in the automatically generated patient-specific anatomical model for which user feedback is required for accurate computation of the hemodynamic index using the one or more trained machine learning models based on extracted features related to the automatically generated patient-specific anatomical model that are input to the one or more trained machine learning models.

4. The method of claim 3, wherein the features include features extracted from the medical image data of the patient.

5. The method of claim 3, wherein the features include non-invasive patient data and measurements acquired for the patient.

6. The method of claim 3, wherein the features include features extracted from the automatically generated patient-specific anatomical model of the one or more arteries of the patient.

7. The method of claim 3, further comprising:
   automatically computing initial values for the hemodynamic index at a plurality of locations in the automatically generated patient-specific anatomical model of the one or more arteries of the patient, wherein the features include the initial values computed for the hemodynamic index at the plurality of locations in the automatically generated patient-specific anatomical model and features extracted from the initial values for the hemodynamic index at the plurality of locations in the automatically generated patient-specific anatomical model.

8. The method of claim 7, wherein automatically computing initial values for the hemodynamic index at a plurality of locations in the automatically generated patient-specific anatomical model of the one or more arteries of the patient comprises:
computing initial values for the hemodynamic index at the plurality of locations in the automatically generated patient-specific anatomical model of the one or more arteries using a second trained machine learning model.

9. The method of claim 3, further comprising:
performing an automated anatomical evaluation of the one or more arteries of the patient in the automatically generated patient-specific anatomical model, wherein the features include anatomical features related to one or more stenosis regions in the one or more arteries of the patient extracted from results of the automated anatomical evaluation of the one or more arteries of the patient in the automatically generated patient-specific anatomical model.

10. The method of claim 1, further comprising:
requesting user feedback for only the regions in the automatically generated patient-specific anatomical model predicted by the one or more trained machine learning models as requiring user feedback for accurate computation of the hemodynamic index;
receiving user feedback for the regions in the automatically generated patient-specific anatomical model predicted by the one or more trained machine learning models as requiring user feedback for accurate computation of the hemodynamic index, resulting in a revised anatomical model of the one or more arteries of the patient; and
computing final values for the hemodynamic index at a plurality of locations in the one or more arteries of the patient based on the revised anatomical model of the one or more arteries of the patient.

11. The method of claim 1, wherein the one or more trained machine learning models include a first trained machine learning model for predicting user feedback requirements at a tree level, a second trained machine learning model for predicting user feedback requirements at a branch level, and a third trained machine learning model for predicting user feedback requirements at a cross-sectional contour level.

12. The method of claim 1, wherein the hemodynamic index is fractional flow reserve.

13. The method of claim 1, wherein the one or more arteries of the patient comprise one or more coronary arteries of the patient.

14. An apparatus for providing fast non-invasive computation of a hemodynamic index from medical image data of a patient, comprising:
a processor; and
a memory storing computer program instructions which when executed by the processor cause the processor to perform operations comprising:
automatically generating a patient-specific anatomical model of one or more arteries of a patient based on medical image data of the patient; and
predicting regions in the automatically generated patient-specific anatomical model for which user feedback is required for accurate computation of a hemodynamic index using one or more trained machine learning models.

15. The apparatus of claim 14, wherein predicting regions in the automatically generated patient-specific anatomical model for which user feedback is required for accurate computation of a hemodynamic index using one or more trained machine learning models comprises:
predicting the regions in the automatically generated patient-specific anatomical model for which user feedback is required for accurate computation of the hemodynamic index using the one or more trained machine learning models based on extracted features related to the automatically generated patient-specific anatomical model that are input to the one or more trained machine learning models.

16. The apparatus of claim 15, wherein the operations further comprise:
automatically computing initial values for the hemodynamic index at a plurality of locations in the automatically generated patient-specific anatomical model of the one or more arteries of the patient, wherein the features include the initial values computed for the hemodynamic index at the plurality of locations in the automatically generated patient-specific anatomical model and features extracted from the initial values for the hemodynamic index at the plurality of locations in the automatically generated patient-specific anatomical model.

17. The apparatus of claim 15, wherein the operations further comprise:
performing an automated anatomical evaluation of the one or more arteries of the patient in the automatically generated patient-specific anatomical model, wherein the features include anatomical features related to one or more stenosis regions in the one or more arteries of the patient extracted from results of the automated anatomical evaluation of the one or more arteries of the patient in the automatically generated patient-specific anatomical model.

18. The apparatus of claim 14, wherein the operations further comprise:
requesting user feedback for only the regions in the automatically generated patient-specific anatomical model predicted by the one or more trained machine learning models as requiring user feedback for accurate computation of the hemodynamic index;
receiving user feedback for the regions in the automatically generated patient-specific anatomical model predicted by the one or more trained machine learning models as requiring user feedback for accurate computation of the hemodynamic index, resulting in a revised anatomical model of the one or more arteries of the patient; and
computing final values for the hemodynamic index at a plurality of locations in the one or more arteries of the patient based on the revised anatomical model of the one or more arteries of the patient.

19. A non-transitory computer readable medium storing computer program instructions for providing fast non-invasive computation of a hemodynamic index from medical image data of a patient, the computer program instructions when executed by a processor cause the processor to perform operations comprising:
automatically generating a patient-specific anatomical model of one or more arteries of a patient based on medical image data of the patient; and
predicting regions in the automatically generated patient-specific anatomical model for which user feedback is required for accurate computation of a hemodynamic index using one or more trained machine learning models.

20. The non-transitory computer readable medium of claim 19, wherein predicting regions in the automatically generated patient-specific anatomical model for which user feedback is required for accurate computation of a hemodynamic index using one or more trained machine learning models comprises:

predicting the regions in the automatically generated patient-specific anatomical model for which user feedback is required for accurate computation of the hemodynamic index using the one or more trained machine learning models based on extracted features related to the automatically generated patient-specific anatomical model that are input to the one or more trained machine learning models.

21. The non-transitory computer readable medium of claim 20, wherein the operations further comprise:

automatically computing initial values for the hemodynamic index at a plurality of locations in the automatically generated patient-specific anatomical model of the one or more arteries of the patient, wherein the features include the initial values computed for the hemodynamic index at the plurality of locations in the automatically generated patient-specific anatomical model and features extracted from the initial values for the hemodynamic index at the plurality of locations in the automatically generated patient-specific anatomical model.

22. The non-transitory computer readable medium of claim 20, wherein the operations further comprise:

performing an automated anatomical evaluation of the one or more arteries of the patient in the automatically generated patient-specific anatomical model, wherein the features include anatomical features related to one or more stenosis regions in the one or more arteries of the patient extracted from results of the automated anatomical evaluation of the one or more arteries of the patient in the automatically generated patient-specific anatomical model.

23. The non-transitory computer readable medium of claim 19, wherein the operations further comprise:

requesting user feedback for only the regions in the automatically generated patient-specific anatomical model predicted by the one or more trained machine learning models as requiring user feedback for accurate computation of the hemodynamic index;

receiving user feedback for the regions in the automatically generated patient-specific anatomical model predicted by the one or more trained machine learning models as requiring user feedback for accurate computation of the hemodynamic index, resulting in a revised anatomical model of the one or more arteries of the patient; and computing final values for the hemodynamic index at a plurality of locations in the one or more arteries of the patient based on the revised anatomical model of the one or more arteries of the patient.

* * * * *